United States Patent
Steinbrenner et al.

(12) 
(10) Patent No.: US 7,956,013 B2
(45) Date of Patent: Jun. 7, 2011

(54) COMPOSITIONS HAVING PH-DEPENDENT VISCOSITY, THICKENER SYSTEMS CONTAINING THE SAME, AND USES THEREFOR

(75) Inventors: Ulrich Steinbrenner, Neustadt (DE); Günter Oetter, Frankenthal (DE); Uwe Ossmer, Houston, TX (US); Marcus Guzmann, Mühlhausen (DE)

(73) Assignee: BASF SE (DE)

( * ) Notice: Subject to any disclaimer, the term of this patent is extended or adjusted under 35 U.S.C. 154(b) by 9 days.

(21) Appl. No.: 12/516,970

(22) PCT Filed: Nov. 29, 2007

(86) PCT No.: PCT/EP2007/063011
§ 371 (c)(1),
(2), (4) Date: May 29, 2009

(87) PCT Pub. No.: WO2008/065172
PCT Pub. Date: Jun. 5, 2008

(65) Prior Publication Data
US 2010/0069268 A1 Mar. 18, 2010

(30) Foreign Application Priority Data
Nov. 30, 2006 (EP) ..................................... 06125152

(51) Int. Cl.
*C09K 8/035* (2006.01)
*C08K 5/49* (2006.01)

(52) U.S. Cl. ........ 507/128; 507/124; 507/136; 510/421; 510/436; 524/81; 524/115; 524/147

(58) Field of Classification Search .................. 507/128, 507/124, 136; 510/421, 436; 524/81, 115, 524/147
See application file for complete search history.

(56) References Cited

U.S. PATENT DOCUMENTS

| 4,293,428 | A | 10/1981 | Gale et al. |
|---|---|---|---|
| 4,360,061 | A | 11/1982 | Canter et al. |
| 4,432,881 | A | 2/1984 | Evani |
| 6,194,356 | B1 | 2/2001 | Jones et al. |
| 7,084,095 | B2 | 8/2006 | Lee et al. |
| 2006/0111248 | A1 | 5/2006 | Lee et al. |
| 2006/0128597 | A1 | 6/2006 | Chen et al. |
| 2008/0081771 | A1 | 4/2008 | Lin et al. |

FOREIGN PATENT DOCUMENTS

| EP | 0225661 A2 | 6/1987 |
|---|---|---|
| GB | 2383355 A | 6/2003 |
| WO | WO-92/08753 A1 | 5/1992 |
| WO | WO-02/11874 A1 | 2/2002 |
| WO | WO-02/102917 A2 | 12/2002 |
| WO | WO-03/056130 A1 | 7/2003 |
| WO | WO-2005/040554 A1 | 5/2005 |
| WO | WO-2005/071038 A1 | 8/2005 |
| WO | WO-2008/065173 A2 | 6/2008 |

*Primary Examiner* — Timothy J. Kugel
(74) *Attorney, Agent, or Firm* — Connolly Bove Lodge & Hutz LLP

(57) ABSTRACT

Compositions comprising: (A) at least one surfactant of the general formula (I)

$$(R^1-[(O-(CH_2)_2)_{x1}(O-CH(CH_3)CH_2)_{x2}]O)_kP(=O)(OH)_{3-k} \quad (I)$$

wherein the sequence of the alkyleneoxy units is arbitrary, each $R^1$ independently represents a moiety selected from the group consisting of linear and branched $C_{12}$-$C_{22}$-alkyl, $C_{12}$-$C_{22}$-alkenyl, $C_{12}$-$C_{22}$-alkynyl, ($C_{11}$-$C_{21}$-alkyl)carbonyl, ($C_{11}$-$C_{21}$-alkenyl)carbonyl and ($C_{11}$-$C_{21}$-alkynyl)carbonyl, k represents 1 or 2 and x1 and x2 each independently represent an integer of 0 to 20, the sum of x1 and x2 being a number of 1 to 20; and (B) at least one thickener comprising at least two hydrophobic groups $R^2$ which are linked to one another via a bridging hydrophilic group ($\alpha$), wherein each $R^2$, independently represents a moiety selected from the group consisting of $C_8$-$C_{32}$-alkyl, $C_8$-$C_{32}$-alkenyl, $C_8$-$C_{32}$-alkynyl, cycloalkyl, aryl, and aryl-$C_1$-$C_{32}$-alkyl, which in each case may have up to 3 hydroxyl substituents; wherein the composition has a pH which is viscosity-dependent.

27 Claims, No Drawings

US 7,956,013 B2

COMPOSITIONS HAVING PH-DEPENDENT VISCOSITY, THICKENER SYSTEMS CONTAINING THE SAME, AND USES THEREFOR

CROSS-REFERENCE TO RELATED APPLICATIONS

This application is a national stage application, under 35 U.S.C. §371, of PCT/EP2007/063011, filed Nov. 29, 2007, which claims priority of European Patent Application No. 06125152.6, filed Nov. 30, 2006.

BACKGROUND OF THE INVENTION

The viscosity of aqueous systems plays a decisive role for a multiplicity of applications. Thickener systems are therefore frequently used in water-based systems, such as, for example, well treatment fluids, cleaner compositions, detergents, formulations for the treatment of leather and textiles, hydraulic fluids, etc., in order to provide the rheological properties required for their specific applications.

WO 92/08753 discloses polymer compounds which are useful as thickeners for aqueous compositions and in particular for latex dispersions.

EP 0 225 661 describes the preparation of gels by crosslinking phosphate esters with polyvalent metal cations, in particular with aluminum ions.

WO 02/102917 describes aqueous compositions which comprise polymers having nonionic, ionic and hydrophobic functional groups, whose viscosity is increased under the action of shear forces or which form a gel under the action of shear forces.

WO 2005/071038 describes compositions and methods for shortening the recovery time of cationic, zwitterionic and amphoteric viscoelastic surfactant compositions after the action of shear forces by addition of three-block oligomers having hydrophilic and hydrophobic moieties, the surfactants preferably having a betaine structure.

US 2006/0128597 describes compositions and methods for shortening the recovery time of cationic, zwitterionic and amphoteric viscoelastic surfactant compositions after the action of shear forces by addition of partly hydrolyzed polyvinyl esters or partly hydrolyzed polyacrylates, the surfactants likewise preferably having a betaine structure.

US 2006/0111248 describes methods for shortening the recovery time of zwitterionic viscoelastic surfactant compositions after the action of shear forces by addition of compounds of the general formula

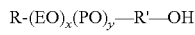

R-(EO)$_x$(PO)$_y$—R'—OH where R is a $C_3$-$C_{18}$-alkyl group, R' is a $C_0$-$C_{14}$-alkylene group, EO is ethyleneoxy and PO is propyleneoxy, the surfactants preferably having a betaine structure.

U.S. Pat. No. 6,194,356 describes well treatment fluids which comprise a viscoelastic surfactant in combination with a crosslinkable, hydrophobically modified polymer.

U.S. Pat. No. 7,084,095 describes the use of encapsulated polymers in an aqueous composition comprising a viscoelastic surfactant, the polymer producing a change in the rheological properties of the aqueous composition under the conditions in the interior of the well.

WO 02/11874 discloses a viscoelastic well treatment fluid which comprise a sufficient amount of an oligomeric surfactant for controlling the viscoelastic properties of the fluid. The monomers of the surfactant used are ionic or zwitterionic compounds which have at least one charged head group and one long-chain hydrophobic hydrocarbon radical.

WO 03/056130 describes aqueous viscoelastic fluids for breaking open rock formations, which comprise a viscoelastic surfactant, especially a betaine, and a hydrophobically modified polymer, the polymer preferably having a molecular weight in the range from $10^4$ to $10^7$ g/mol.

WO 2005/040554 describes methods for increasing the viscosity of viscoelastic surfactant compositions for the treatment of wells by addition of hydrophilic-lipophilic organic compounds, such as, for example, alkyl alcohols, alkylthiols or alkylamines.

In many of the possible fields of use of thickener systems, the high viscosity of the aqueous compositions which is required for the special application prove to be problematic, for example in the placing or the subsequent removal of the composition. Particularly in the treatment of poorly accessible areas with relatively high-viscosity compositions, it is desirable to be able to reduce the viscosity of the composition after treatment is complete, in order to facilitate complete removal of the composition. An example of this is in particular the use of relatively high-viscosity treatment fluids in the development and maintenance of wells.

For these applications and a multiplicity of other applications, it is advantageous to use compositions whose viscosity can be varied by a simple method. None of the abovementioned documents describes such compositions which make it possible to vary the viscosity under the respective conditions of use.

BRIEF SUMMARY OF THE INVENTION

The present invention relates to compositions having a pH-dependent viscosity, which are useful for use as thickener systems for aqueous compositions, especially in the area of the development and extraction of mineral oil and natural gas deposits.

It is therefore the object of the present application to provide compositions whose use in aqueous compositions ensures simple and targeted variation of the rheological properties, in particular of the viscosity, under the given conditions of use in each case.

Surprisingly, it was found that the rheological properties of aqueous compositions can be varied via the pH by the use of the compositions described below.

The present invention therefore relates to a composition comprising (A) at least one surfactant of the general formula (I)

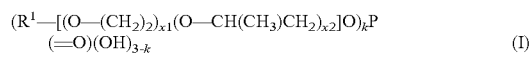

$$(R^1-[(O-(CH_2)_2)_{x1}(O-CH(CH_3)CH_2)_{x2}]O)_k P(=O)(OH)_{3-k} \quad (I)$$

where the sequence of the alkyleneoxy units is arbitrary, $R^1$ is selected from linear and branched $C_{12}$-$C_{22}$-alkyl, $C_{12}$-$C_{22}$-alkenyl, $C_{12}$-$C_{22}$-alkynyl, ($C_{11}$-$C_{21}$-alkyl)carbonyl, ($C_{11}$-$C_{21}$-alkenyl)carbonyl and ($C_{11}$-$C_{21}$-alkynyl)carbonyl, k is 1 or 2 and $x^1$ and $x^2$, independently of one another, are an integer from 0 to 20, the sum of $x^1$ and $x^2$ being a number from 1 to 20; and (B) at least one thickener comprising at least two hydrophobic groups $R^2$ which are linked to one another via a bridging hydrophilic group (α), where the radicals $R^2$, independently of one another, are selected from $C_8$-$C_{32}$-alkyl, $C_8$-$C_{32}$-alkenyl, $C_8$-$C_{32}$- alkynyl, cycloalkyl, aryl or aryl-$C_1$-$C_{32}$-alkyl, which in each case may have 1, 2 or 3 hydroxyl substituents.

In the context of the present invention, the expression alkyl comprises straight-chain and branched alkyl groups. Suitable short-chain alkyl groups are, for example, straight-chain or branched $C_1$-$C_{10}$-alkyl groups, specifically $C_1$-$C_7$-alkyl groups, preferably $C_1$-$C_6$-alkyl groups and particularly preferably $C_1$-$C_4$-alkyl groups. These include in particular methyl, ethyl, propyl, isopropyl, n-butyl, 2-butyl, sec-butyl, tert-butyl, etc.

In the context of the present invention, the expression $C_{11}$-$C_{22}$-alkyl comprises straight-chain and branched alkyl groups. These are preferably straight-chain and branched $C_{15}$-$C_{20}$-alkyl radicals. In particular, they are predominantly linear alkyl radicals as also occur in natural or synthetic fatty acids and fatty alcohols and oxo alcohols. These include, for example, n-undecyl, n-dodecyl, n-tridecyl, myristyl, pentadecyl, palmityl (=cetyl), heptadecyl, octadecyl, nonadecyl, arrachinyl (arachidyl), behenyl, etc.

In the context of the present invention, $C_8$-$C_{32}$-alkenyl, specifically $C_{11}$-$C_{22}$-alkenyl, represents straight-chain and branched alkenyl groups which may be mono-, di- or polyunsaturated. These are preferably $C_{15}$-$C_{20}$-alkenyl. In particular, they are predominantly linear alkenyl radicals, as also occur in natural or synthetic fatty acids and fatty alcohols and oxo alcohols. These include in particular octenyl, nonenyl, decenyl, undecenyl, dodecenyl, tridecenyl, tetradecenyl, pentadecenyl, hexadecenyl, heptadecenyl, octadecenyl, nonadecenyl, linolyl, linolenyl, eleostearyl etc. and in particular oleyl (9-octadecenyl).

In the context of the present invention, $C_9$-$C_{32}$-alkynyl, specifically $C_{11}$-$C_{22}$-alkynyl, represents straight-chain and branched alkynyl groups which may be mono-, di- or polyunsaturated. They are preferably $C_{15}$-$C_{20}$-alkynyl. In particular they are predominantly linear alkynyl radicals.

In the context of the present invention, the expression $C_{11}$-$C_{21}$-alkylcarbonyl comprises straight-chain or branched alkyl groups, as defined above, which are linked via a carbonyl group (—C(=O)—). The expressions $C_{11}$-$C_{21}$-alkenylcarbonyl and $C_{11}$-$C_{21}$-alkynylcarbonyl are analogous.

In the context of the present invention, the expression "cycloalkyl" comprises an unsubstituted as well as a substituted monocyclic or bicyclic saturated hydrocarbon group having in general 3 to 6, 8, 10, 12, or 15 carbon ring members, such as $C_3$-$C_{15}$-cycloalkyl, e.g. cyclopropyl, cyclobutyl, cyclopentyl, cyclohexyl, cycloheptyl, cyclooctyl, or $C_7$-$C_{12}$-bicycloalkyl.

In the context of the present invention, the expression "aryl" comprises a mono-, di- or trinuclear aromatic ring system, comprising 6 to 14 carbon ring members which ring system may be unsubstituted or substituted, e.g. phenyl, naphthyl and anthracenyl. A mono- or dinuclear ring system, such as phenyl or naphthyl, is preferred and a mononuclear aromatic ring system, phenyl, is particularly preferred.

In the context of the present invention, the expression rheological properties is widely interpreted and means both viscosity and elasticity, but preferably viscosity.

DETAILED DESCRIPTION OF THE INVENTION

Preferably, the radicals $R^1$ of the surfactants of the general formula (I) which are present in the composition have on average not more than one, particularly preferably not more than 0.5 and in particular not more than 0.2 branch. In particular, the radicals $R^1$, independently of one another, are selected from palmityl, stearyl, oleyl, linoleyl, arachidyl, gadoleyl, behenyl, erucyl, isostearyl, 2-hexyldecyl, 2-heptyldecyl, 2-heptylundecyl and 2-octyldodecyl.

The surfactants present in the composition according to the invention have one or two (poly)alkyleneoxy groups which consist of $x^1$ ethyleneoxy and $x^2$ propyleneoxy groups, which may be linked to one another in any desired sequence.

Preferably, the sum of $x^1$ and $x^2$, averaged over the surfactants of the general formula (I) which are present, is in the range from 1 to 10 and particularly preferably in the range from 3 to 9. In particular, each surfactant of the general formula (I) which is present in the composition has a value in the range from 1 to 10 and particularly preferably a value in the range from 3 to 9 for the sum of $x^1$ and $x^2$.

The ratio of $x^1$ to $x^2$, averaged over the surfactants of the general formula (I) which are present, is preferably at least 2:1. In a special embodiment of the composition according to the invention, the (poly)alkyleneoxy groups of the surfactants of the general formula (I) consist exclusively of ethyleneoxy units. Thus, $x^2$ is in particular 0.

Surfactants of the general formula (I) which are used according to the invention are provided, for example, by reaction of phosphoric acid or a suitable phosphoric acid derivative, such as, for example, $P_2O_5$, $P_4O_{10}$, polyphosphoric acid ($H_3PO_4.(HPO_3)_n$ where n>1) or metaphosphoric acid (($HPO_3)_n$ where n>3), with a suitable alkoxylated alcohol of the formula $R^1$—[(O—(CH_2)_2)_{x1}(O—CH(CH_3)CH_2)_{x2}]—OH or mixtures of these alkoxylated alcohols, as are obtained in particular by reaction of natural or synthetic mixtures of fatty alcohols or oxo alcohols with ethylene oxide and/or propylene oxide. In addition to inorganic phosphoric acids, mixtures of mono- and diphosphoric acid esters of the general formula (I) are obtained here.

The composition according to the invention preferably comprises, as surfactants of the general formula (I), at least one phosphoric acid monoester of the general formula (I.a)

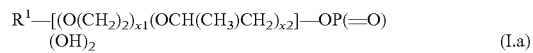

$$R^1—[(O(CH_2)_2)_{x1}(OCH(CH_3)CH_2)_{x2}]—OP(=O)(OH)_2 \quad \text{(I.a)}$$

where the sequence of the alkyleneoxy units is arbitrary and the abovementioned preferences apply with regard to $R^1$, $x^1$ and $x^2$. Preferably at least 50%, particularly preferably at least 80% and in particular at least 90% of the surfactants of the general formula (I) which are present are selected from compounds of the general formula (I.a).

The compositions according to the invention advantageously comprise an amount in the range from 0.1 to 99.9% by weight, preferably from 0.5 to 60% by weight and particularly preferably from 1 to 40% by weight of surfactants of the general formula (I), based on the total weight of the components of the composition according to the invention which differ from water.

In order to ensure a sufficiently high viscosity over a wide temperature range, for example from 25 to 70° C., the molar amount of the compounds of the general formula (I) is advantageously chosen so that, based on the total composition according to the invention, a ratio of from 2 to 20, preferably from 3 to 12, alkyleneoxy units per phosphorus atom results.

The compositions according to the invention comprise, as thickener (B), at least one compound comprising at least two hydrophobic radicals $R^2$ which are linked to one another via a bridging hydrophilic group (α).

The hydrophobic groups $R^2$ preferably comprise on average at least 14 and in particular at least 16 carbon atoms. The upper limit of the number of carbon atoms is as a rule not critical and is, for example, up to 100, preferably up to 50 and in particular up to 35. Particularly preferably, less than 10% of the hydrophobic groups $R^2$ present in the thickeners (B) comprise less than 15 and more than 23 carbon atoms.

Preferably, on average less than 20% and in particular less than 5% of the groups $R^2$ present have a carbon-carbon double bond.

The hydrophobic groups $R^2$ are preferably selected from linear or branched $C_{12}$-$C_{22}$-alkyl, $C_{12}$-$C_{22}$-alkenyl or 2-hydroxy($C_{12}$-$C_{22}$-alk-1-yl).

The radicals $R^2$ of the thickeners (B) present in the composition according to the invention have on average preferably not more than one, particularly preferably not more than 0.5 and in particular not more than 0.2 branch. In particular, the radicals $R^2$, independently of one another, are selected from palmityl, stearyl, oleyl, linoleyl, arachidyl, gadoleyl, behenyl, erucyl, isostearyl, 2-hexyldecyl, 2-heptyldecyl, 2-heptylundecyl, 2-octyldodecyl and 2-hydroxypalmityl, 2-hydroxystearyl, 2-hydroxyoleyl, 2-hydroxylinoleyl, 2-hydroxyarachidyl, 2-hydroxygadoleyl, 2-hydroxybehenyl, 2-hydroxyerucyl and 2-hydroxyisostearyl.

Preferably at least 70% of the groups $R^2$ present in the thickeners (B) are straight-chain.

In a special embodiment, hydrophilic groups ($\alpha$) which comprise at least two hydrophilic units ($\beta$) are used. The hydrophilic units ($\beta$) may have identical or different meanings. Identical hydrophilic units ($\beta$) are always linked to one another via a bridging group ($\gamma$). Different hydrophilic units ($\beta$) can be linked to one another directly or via a bridging group ($\gamma$).

In a preferred embodiment of the present invention, the bridging hydrophilic group ($\alpha$) comprises polyether units and/or polyvinyl alcohol units as hydrophilic units ($\beta$). Particularly preferably, the bridging hydrophilic group ($\alpha$) comprises at least 90% of polyether units.

In a special embodiment of the present invention, the hydrophilic units ($\beta$) of the thickeners (B) present in the composition according to the invention are at least partly selected from polyether units of the general formula (II)

$$—[(O—CH_2)_2)_{y1}(O—CH(CH_3)CH_2)_{y2}]—\qquad(II)$$

where the sequence of the alkyleneoxy units is arbitrary and $y^1$ and $y^2$, independently of one another, are an integer from 0 to 300, the sum of $y^1$ and $y^2$ being a number from 10 to 300.

The sum of $y^1$ and $y^2$ designates the number of alkyleneoxy units of this polyether chain and, averaged over all polyether units of the formula (II) which are present, preferably has a value in the range of from 20 to 200, particularly preferably from 30 to 150.

The ratio of $y^1$ to $y^2$ expresses the ratio of ethyleneoxy to propyleneoxy units. Averaged over the polyether chains of the general formula (II) which are present, the ratio of $y^1$ to $y^2$ is preferably at least 2:1, particularly preferably at least 5:1.

Different hydrophilic polyether units are preferably linked to one another without bridging groups ($\gamma$). These include, for example, EO/PO block copolymer units.

In a special embodiment of the present invention, the polyether chain of the formula (II) consists exclusively of ethyleneoxy units. In this embodiment, $y^2$ is 0.

In a further special embodiment of the present invention, the hydrophilic groups ($\alpha$) are composed of hydrophilic units ($\beta$) which are linked to one another via bridging groups ($\gamma$), the bridging groups ($\gamma$) differing structurally from the repeating units of which the hydrophilic units ($\beta$) are composed.

The bridging groups ($\gamma$) between the hydrophilic units ($\square$) of the thickeners (B) present in the composition according to the invention are preferably selected from m-valent, preferably divalent to tetravalent, groups, with 1 to 10 bridge atoms between the flanking bonds, the co-valent group having structural units which are selected from —OC(=O)—, —C(=O)OC(=O)—, —OC(=O)O—, —OC(=O)NH—, alkylene, alkenylene, arylene, heterocyclylene and cycloalkylene, it being possible for alkylene and alkenylene to be interrupted once or several times by oxygen, sulfur, —NH— and —N($C_1$-$C_{10}$-alkyl)-, it being possible for arylene, heterocyclylene and cycloalkylene to be mono- or polysubstituted by $C_1$-$C_4$-alkyl and m being a number in the range from 2 to 4. The bridging groups ($\gamma$) preferably have —OC(=O)NH— as terminal structural units.

In this context, the term "m-valent group" means that the bridging group ($\gamma$) is capable of forming m chemical bonds, where m is an integer and is preferably 2, 3 or 4.

If alkylene or alkenylene is interrupted by one or more, for example 1, 2, 3, 4, 5, 6, 7 or 8, non-neighboring groups which, independently of one another, are selected from oxygen, sulfur, —NH— and N($C_1$-$C_{10}$-alkyl)-, the termini of the alkylene or alkenylene group are formed by carbon atoms. Examples of these are —(CH$_2$)$_3$N(CH$_3$)CH$_2$—, —(CH$_2$)$_3$N(C$_2$H$_5$)(CH$_2$)—, —(CH$_2$)$_3$—OCH$_2$—, —(CH$_2$)$_3$—O—CH(CH$_3$)CH$_2$—, —(CH$_2$)$_2$—O(CH$_2$)$_2$—OCH$_2$—, —CH$_2$—(CH$_2$)$_2$—CH$_2$—N(CH$_3$)(CH$_2$)$_3$—, —CH$_2$)$_2$N[CH(CH$_3$)$_2$]CH$_2$—, —(CH$_2$)$_2$—N(C$_2$H$_5$)CH$_2$—, —(CH$_2$)$_2$N(CH$_3$)CH$_2$—, —CH$_2$)$_2$OCH$_2$—, —(CH$_2$)$_2$OCH$_2$CH$_2$—, —(CH$_2$)$_3$—SCH$_2$—, —(CH$_2$)$_3$—S—CH(CH$_3$)CH$_2$—, —(CH$_2$)$_2$S(CH$_2$)$_2$—SCH$_2$—, —(CH$_2$)$_2$SCH$_2$— and —(CH$_2$)$_2$SCH$_2$CH$_2$—.

If the m-valent group ($\gamma$) has a valency greater than 2, this permits branching of the thickener (B). In this case, the thickener (B) may also comprise more than two hydrophobic groups $R^2$.

(B) preferably comprises from two to six, particularly preferably from two to four, hydrophobic groups $R^2$.

The preferred range for the molecular weight of the thickeners (B) present is obtained by multiplying the number of hydrophobic groups $R^2$ present by a value of from 1500 to 8000 g/mol.

The thickeners (B) present in the composition according to the invention preferably have on average a molecular weight in the range from 3000 to 50 000 g/mol, particularly preferably in the range from 5000 to 30 000 g/mol.

The compositions according to the invention advantageously comprise an amount in the range of from 0.1 to 50% by weight, preferably from 0.5 to 30% by weight and particularly preferably from 1 to 20% by weight of thickener (B), based on the total weight of the components different from water in the composition according to the invention.

Thickeners (B) used according to the invention can be provided, for example, by reaction of polyisocyanates, polyols, polyamines, or polycarboxylic acids with a suitable alkoxylated alcohol, such as, for example, an alkoxylated alcohol of the formula $R^2$—[(O—(CH$_2$)$_2$)$_{y1}$(O—CH(CH$_3$)CH$_2$)$_{y2}$]—OH or mixtures of these alkoxylated alcohols. These alcohols are provided in particular by reaction of natural or synthetic mixtures of fatty alcohols and oxo alcohols with ethylene oxide and/or propylene oxide. Mixtures of alcohols having different numbers of alkyleneoxy units are usually obtained thereby and can be used as such. The thickeners (B) used according to the invention can likewise be provided by reacting compounds which comprise at least two different functional groups with the abovementioned alcohols.

The thickeners (B) are preferably provided starting from polyisocyanates or polyols.

Suitable polyisocyanates, in particular diisocyanates and triisocyanates, for the provision of thickeners (B) are the aliphatic, cycloaliphatic, araliphatic and aromatic di- or polyisocyanates mentioned below by way of example. 4,4'-Diphenylmethane diisocyanate, the mixtures of monomeric diphenylmethane diisocyanates and oligomeric diphenylmethane diisocyanates (polymer MDI), tetramethylene diisocyanate, tetramethylene diisocyanate trimers, hexamethylene diisocyanate, hexamethylene diisocyanate trimers, isophorone diisocyanate trimer, 4,4'-methylenebis(cyclohexyl) diisocyanate, xylylene diisocyanate, tetramethylxylylene diisocyanate, dodecyl diisocyanate, lysine alkyl ester diisocyanate, alkyl being $C_1$-$C_{10}$-alkyl, 1,4-diisocyanatocyclohexane or 4-isocyanatomethyl-1,8-octamethylene diisocyanate may preferably be mentioned here, particularly preferably hexamethylene diisocyanate and 4,4'-diphenylmethane diisocyanate.

Suitable diols for the provision of (B) are straight-chain and branched, aliphatic and cycloaliphatic alcohols having in general about 2 to 30, preferably about 2 to 20, carbon atoms. These include 1,2-ethanediol, 1,2-propanediol, 1,3-propanediol, 1,2-butanediol, 1,3-butanediol, 1,4-butanediol, 2,3-butanediol, 1,2-pentanediol, 1,3-pentanediol, 1,4-pentanediol, 1,5-pentanediol, 2,3-pentanediol, 2,4-pentanediol, 1,2-hexanediol, 1,3-hexanediol, 1,4-hexanediol, 1,5-hexanediol, 1,6-hexanediol, 2,5-hexanediol, 1,2-heptanediol, 1,7-heptanediol, 1,2-octanediol, 1,8-octanediol, 1,2-nonanediol, 1,9-nonanediol, 1,2-decanediol, 1,10-decanediol, 1,12-dodecanediol, 2-methyl-1,3-propanediol, 2-methyl-2-butyl-1,3-propanediol, 2,2-dimethyl-1,3-propanediol, 2,2-dimethyl-1,4-butanediol, pinacol, 2-ethyl-2-butyl-1,3-propanediol, diethylene glycol, triethylene glycol, dipropylene glycol, tripropylene glycol, polyalkylene glycols, cyclopentanediols, cyclohexanediols, etc.

Suitable triols for the provision of (B) are, for example, glycerol, butane-1,2,4-triol, n-pentane-1,2,5-triol, n-pentane-1,3,5-triol, n-hexane-1,2,6-triol, n-hexane-1,2,5-triol, trimethylolpropane, trimethylolbutane. Suitable triols are furthermore the triesters of hydroxycarboxylic acids with trihydric alcohols. These are preferably triglycerides of hydroxycarboxylic acids, such as, for example, lactic acid, hydroxystearic acid and ricinoleic acid. Naturally occurring mixtures which comprise hydroxycarboxylic acid triglycerides are also suitable, in particular castor oil. Preferred triols are glycerol and trimethylenepropane.

Suitable polyols having a higher functionality for the provision of (B) are, for example, sugar alcohols and derivatives thereof, such as erythritol, pentaerythritol, dipentaerythritol, threitol, inositol and sorbitol. Reaction products of the polyols with alkylene oxides, such as ethylene oxide and/or propylene oxide, are also suitable. It is also possible to use higher molecular weight polyols having a number average molecular weight in the range from about 400 to 6000 g/mol, preferably from 500 to 4000 g/mol. These include, for example, polyesterols based on aliphatic, cycloaliphatic and/or aromatic di-, tri- and/or polycarboxylic acids with di-, tri- and/or polyols and also the lactone-based polyesterols. These furthermore include polyetherols which are obtainable, for example, by polymerization of cyclic ethers or by reaction of alkylene oxides with an initiator molecule. These furthermore include customary polycarbonates known to the person skilled in the art and having terminal hydroxyl groups, which are obtainable by reaction of the above-described diols or of bisphenols, such as bisphenol A, with phosgene or carboxylic acid diesters. $\alpha,\omega$-Polyamidols, $\alpha,\omega$-polymethyl (meth)acrylate diols and/or $\alpha,\omega$-polybutyl (meth)acrylate diols, such as, for example, MD-1000 and BD-1000 from Goldschmidt, are also suitable.

Suitable dicarboxylic acids for the provision of (B) are, for example, oxalic acid, malonic acid, succinic acid, glutaric acid, adipic acid, pimelic acid, suberic acid, azelaic acid, sebacic acid, undecane-$\alpha,\omega$-dicarboxylic acid, dodecane-$\alpha,\omega$-dicarboxylic acid, cis- and trans-cyclohexane-1,2-dicarboxylic acid, cis- and trans-cyclohexane-1,3-dicarboxylic acid, cis- and trans-cyclohexane-1,4-dicarboxylic acid, cis- and trans-cyclopentane-1,2-dicarboxylic acid, cis- and trans-cyclopentane-1,3-dicarboxylic acid, phthalic acid, isophthalic acid, terephthalic acid and mixtures thereof.

The abovementioned dicarboxylic acids may also be substituted. Suitable substituted dicarboxylic acids may have one or more radicals which are preferably selected from alkyl, cycloalkyl and aryl, as defined at the outset. Suitable substituted dicarboxylic acids are, for example, 2-methylmalonic acid, 2-ethylmalonic acid, 2-phenylmalonic acid, 2-methylsuccinic acid, 2-ethylsuccinic acid, 2-phenylsuccinic acid, itaconic acid, 3,3-dimethylglutaric acid, etc.

Dicarboxylic acids can be used either as such or in the form of derivatives. Suitable derivatives are anhydrides and oligomers and polymers thereof, mono- and diesters, preferably mono- and dialkyl esters, and acid halides, preferably chlorides. Suitable esters are mono- or dimethyl esters, mono- or diethyl esters, and mono- and diesters of higher alcohols, such as, for example, n-propanol, isopropanol, n-butanol, isobutanol, tert-butanol, n-pentanol, n-hexanol, etc., and furthermore mono- and divinyl esters and mixed esters preferably methylethyl esters.

Preferred polycarboxylic acids for the provision of the thickeners (B) are succinic acid, glutaric acid, adipic acid, phthalic acid, isophthalic acid, terephthalic acid or the mono- or dimethyl esters thereof. Adipic acid is particularly preferred.

Suitable polyamines are, for example, ethylenediamine, propylenediamine, diethylenetriamine, triethylenetetramine, tetraethylenepentamine, polyethylenimine, 1,3-propanediamine, N,N-bis(aminopropyl)amine, N,N,N-tris(aminoethyl)amine, N,N,N',N'-tetrakis(aminoethyl)ethylenediamine, N,N,N',N'',N''-pentakis(aminoethyl)diethylenetriamine, neopentanediamine, hexamethylenediamine, octamethylenediamine or isophoronediamine.

Other compounds suitable for the provision of the thickeners (B) are compounds which comprise at least two different functional groups, such as, for example, ethanolamine, N-methylethanolamine, propanolamine, hydroxyacetic acid, lactic acid, glutamic acid and aspartic acid.

In a particularly preferred embodiment, the thickener (B) is provided starting from (a) $C_{14}$-$C_{22}$-fatty alcohol ethoxylates and mixtures thereof, (b) polyethylene glycol, EO-PO copolymers, trimethylolpropane ethoxylates/trimethylol propoxylates, glyceryl ethoxylates/propoxylates and mixtures thereof and (c) hexamethylene diisocyanate.

In a further particularly preferred embodiment, the thickener (B) is provided starting from (a) polyethylene glycol, EO-PO copolymers, trimethylolpropane ethoxylates/trimethylol propoxylates, glyceryl ethoxylates/propoxylates and mixtures thereof and (b) 1,2-epoxy-$C_{14}$-$C_{22}$-alkanes and mixtures thereof.

The compositions according to the invention may comprise further components in addition to the surfactants of the general formula (I) and the thickener.

In a preferred embodiment of the present invention, the composition additionally comprises at least one linear or branched $C_6$-$C_{15}$-monoalcohol (C). The monoalcohols preferably have not more than one branch. If a plurality of $C_6$-$C_{18}$-monoalcohols (C) are present in the composition according to the invention, they have on average preferably not more than 0.5 and particularly preferably not more than 0.2 branch.

Preferred $C_6$-$C_{18}$-monoalcohols (C) are, for example, n-hexanol, n-heptanol, n-octanol, n-nonanol, n-decanol, n-undecanol and n-dodecanol.

In this preferred embodiment, the compositions according to the invention advantageously comprise an amount in the range from 0.1 to 20% by weight, preferably from 0.5 to 15% by weight and particularly preferably from 1 to 8% by weight of $C_6$-$C_{18}$-monoalcohols (C), based on the total weight of the components differing from water in the composition according to the invention.

In a special embodiment, the composition according to the invention additionally comprises at least one nonionic surfactant (D) of the general formula (III) where

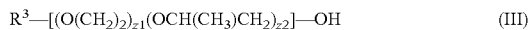   (III)

where
the sequence of the alkyleneoxy units is arbitrary,
$R^3$ is selected from $C_{12}$-$C_{22}$-alkyl, $C_{12}$-$C_{22}$-alkenyl, $C_{12}$-$C_{22}$-alkynyl, ($C_{11}$-$C_{21}$-alkyl)carbonyl, ($C_{11}$-$C_{21}$-alkenyl)carbonyl and ($C_{11}$-$C_{21}$-alkynyl)carbonyl
and
$z^1$ and $z^2$, independently of one another, are an integer from 0 to 20, the sum of $z^1$ and $z^2$ being a number from 1 to 20.

The radicals $R^3$ of the nonionic surfactants of the general formula (III) which are present in the composition preferably have on average not more than one, particularly preferably not more than 0.5 and in particular not more than 0.2 branch. In particular, the radicals $R^3$, independently of one another, are selected from palmityl, stearyl, oleyl, linoleyl, arachidyl, gadoleyl, behenyl, erucyl, isostearyl, 2-hexyldecyl, 2-heptyldecyl, 2-heptylundecyl and 2-octyldodecyl.

The nonionic surfactants (D) present in the composition according to the invention have a (poly)alkyleneoxy group which consists of $z^1$ ethyleneoxy and $z^2$ propyleneoxy groups linked to one another in any desired sequence.

Nonionic surfactants of the general formula (III) which are used according to the invention are provided, for example, by reaction of natural or synthetic mixtures of fatty alcohols and oxo alcohols with ethylene oxide and/or propylene oxide. Mixtures of compounds of the formula (III) having differing numbers of alkyleneoxy units are usually obtained thereby. These can be used as mixtures in the compositions according to the invention.

The sum of $z^1$ and $z^2$, averaged over the compounds of the general formula (III) which are present, is preferably in the range from 1 to 10 and particularly preferably in the range from 3 to 9. In particular, each nonionic surfactant of the general formula (III) which is present in the composition has a value in the range from 1 to 10 and particularly preferably a value in the range from 3 to 9 for the sum of $z^1$ and $z^2$.

The ratio of $z^1$ to $z^2$, averaged over the nonionic surfactants of the general formula (III) which are present, is preferably at least 2:1. In a special embodiment of the composition according to the invention, the (poly)alkyleneoxy groups of the surfactants of the general formula (I) consist exclusively of ethyleneoxy units. Thus, $z^2$ is in particular 0.

In a further special embodiment, the composition according to the invention additionally comprises at least one water-miscible solvent (E) differing from the $C_6$-$C_{18}$-monoalcohols (C). The solvent (E) preferably has a molecular weight of less than 400 g/mol.

Suitable water-miscible solvents (E) are, for example, homo- and heterooligomers of ethylene oxide and/or propylene oxide, e.g. ethylene glycol or propylene glycol, alcohols, e.g. methanol, ethanol, isopropanol, butylmonoglycol, butyldiglycol, butyltriglycol, phenoxyethanol, phenoxypropanol or o-sec-butylphenol, N-alkylpyrrolidones, for example N—($C_1$-$C_4$-alkyl)pyrrolidones such as N-methylpyrrolidone, and alkylene carbonates, for example $C_2$-$C_4$-alkylene carbonates, such as ethylene carbonate.

In a further special embodiment, the composition according to the invention additionally comprises at least one water-soluble base (F).

Suitable water-soluble bases (F) are, for example, alkali metal and alkaline earth metal salts, e.g. NaOH, $Na_2CO_3$, $NaHCO_3$, KOH, $K_2CO_3$, $KHCO_3$ or $Ca(OH)_2$, and amines, e.g. triethanolamine or dialkylmonoethanolamines, such as di-($C_1$-$C_4$-alkyl)monoethanolamines.

Depending on the intended use, the compositions according to the invention can optionally comprise further components, such as, for example, salts, metal oxide particles, complexing agents, acids, biocides or antifreezes.

The compositions according to the invention or the aqueous compositions which comprise them are distinguished by a pH dependence of their viscosity. Thus, the pH can be used to control whether the composition according to the invention is present in the form of a low-viscosity liquid or a higher-viscosity liquid or in the form of a gel. Owing to these advantageous rheological properties, the compositions according to the invention are suitable as thickener systems for a multiplicity of applications.

The present invention therefore furthermore relates to the use of a composition according to the invention for controlled adjustment of the rheological properties of aqueous compositions.

The compositions according to the invention are particularly preferably used in fluids which are employed in the development and/or exploitation of underground mineral oil and/or natural gas deposits. They serve for adjusting the theological properties of these fluids. These fluids are, for example, treatment fluids for breaking open rock formations, for acid treatment of rock formations (acidizing), for use during drilling, for workover, for redirecting streams, for controlling the permeability or for blocking off water. They are preferably acid gelling agents or drilling fluids.

In the context of the present invention, the term treatment fluid is used in general for aqueous compositions which are intended to be present in relatively highly viscous form during the treatment. In general, they have a pH in the acidic range during the treatment. For removing the treatment fluids from the treatment point, in particular in the case of poorly accessible treatment points, said fluids should have as low a viscosity as possible after treatment is complete. The reduction of the viscosity can be achieved with the use of the compositions according to the invention, by increasing the pH.

Advantageously, the abovementioned treatment fluids have a viscosity in the range from 50 to 100 mPa·s at a shear rate of 100 s$^{-1}$ during the treatment.

The abovementioned viscosity ranges of the treatment fluids are achieved with the use of the compositions according to the invention, usually at a pH in the range from 2 to 6 and in particular in the range from 3 to 5.

Depending on the concentration of the components present therein, the compositions according to the invention make it possible, when used in a small amount, to keep the viscosity of the treatment fluids in the required viscosity range during the treatment over a wide temperature range.

The aqueous treatment fluids preferably comprise the compositions according to the invention in an amount of from 0.1 to 30% by weight, particularly preferably from 0.2 to 15% by weight and in particular from 0.5 to 5% by weight, based on the total weight of the treatment fluid.

After treatment is complete, the abovementioned treatment fluids advantageously have a viscosity of <10 mPa·s and particularly preferably <5 mPa·s at a shear rate of 100 s$^{-1}$. The reduction of the viscosity is effected with the use of the compositions according to the invention in general by increasing the pH to a value of at least 7.

As is known to the person skilled in the art, the pH can be increased by adding a suitable base, such as, for example, NaOH, KOH, Ca(OH)$_2$ or CaO. In a special embodiment, the pH is increased by contact between the acidic components of the treatment fluid and basic components of the rock formations.

The present invention furthermore relates to a process for the treatment of underground rock formations using a composition according to the invention as a thickener system, in particular for use in acid gelling agents and/or drilling fluid.

In the context of the present invention, the term acid gelling agent is used for acidic, relatively highly viscous treatment fluids which are used for acid treatments of underground rock formations. With the use of the compositions according to the invention in such acid gelling agents, the pH of the acid gelling agent is gradually increased by the action on basic constituents of the rock formations, until a pH which leads to breaking up of the gel and hence to a reduction in the viscosity is reached. The special advantage of using compositions according to the invention here is therefore that, after the end of the action of the gelled acid, the viscosity is reduced without external intervention and hence the removal of the treatment fluid is facilitated.

In the context of the present invention, the term drilling fluid is used for relatively highly viscous treatment fluids which are used during the drilling process for flushing the well.

The present invention furthermore relates to the use of a composition according to the invention for adjusting the rheological properties of detergents and cleaning agents.

Detergents and cleaning agents comprise at least one liquid or solid carrier and, if appropriate, customary additives, in addition to the compositions according to the invention.

Examples of suitable additives comprise:
- Builders and cobuilders, for example polyphosphates, zeolites, polycarboxylates, phosphonates, citrates, complexing agents,
- Ionic surfactants, for example alkylbenzenesulfonates, α-olefinsulfonates and other alcohol sulfates/ether sulfates, sulfosuccinates,
- Other nonionic surfactants, for example alkylaminoalkoxylates and alkylpolyglucosides, amphoteric surfactants, e.g. alkylamine oxides, betaines,
- Optical brighteners,
- Color transfer inhibitors, e.g. polyvinylpyrrolidone,
- Standardizing agents, e.g. sodium sulfate, magnesium sulfate,
- Soil release agents, e.g. polyethers/polyesters, carboxymethylcellulose,
- Incrustation inhibitors, e.g. polyacrylates, copolymers of acrylic acid and maleic acid,
- Bleach systems consisting of bleaches, e.g. perborate or percarbonate, plus bleach activators, e.g. tetraacetylethylenediamine, plus bleach stabilizers,
- Perfume,
- Foam inhibitors, e.g. silicone oils, alcohol propoxylates (especially in liquid detergents),
- Enzymes, e.g. amylases, lipases, proteases or carboxylases,
- Alkali donors, e.g. pentasodium metasilicate or sodium carbonate.

Further constituents known to the person skilled in the art may likewise be present.

Liquid detergents may additionally comprise solvents, e.g. ethanol, isopropanol, 1,2-propylene glycol or butylene glycol.

Gel-like detergents additionally comprise thickeners, such as, for example, polysaccharides and slightly crosslinked polycarboxylates (e.g. the Carbopol® brands from BF Goodrich).

In the case of detergents in tablet form, further additives are required. These are, for example, tableting assistants, e.g. polyethylene glycols having molar masses of >1000 g/mol or polymer dispersions. Tablet disintegrants, e.g. cellulose derivatives, crosslinked polyvinlpyrrolidone, crosslinked polyacrylates or combinations of acids, e.g. citric acid, with sodium carbonate, are also required.

In cleaners for hard surfaces, e.g. acidic cleaners, neutral cleaners, machine dishwashing, metal degreasing, glass cleaners, floor cleaners, to name but a few, the compositions according to the invention are used in combination with the additives mentioned below, which are present in amounts of from 0.01 to 40% by weight, preferably from 0.1 to 20% by weight.

- Ionic surfactants, such as, for example, alkylbenzenesulfonates, α-olefinsulfonates, other alcohol sulfates/ether sulfates, sulfosuccinates
- Other nonionic surfactants, e.g. alkylamine alkoxylates and alkyl polyglucosides, also the $C_{13}$-$C_{15}$-alkylpolyglucosides according to the invention
- Amphoteric surfactants, e.g. alkylamine oxides, betaines
- Builders, e.g. polyphosphates, polycarboxylates, polyphosphonates, complexing agents
- Dispersants, e.g. naphthalenesulfonic acid condensates, polycarboxylates,
- Enzymes, e.g. lipases, amylases, proteases, carboxylases,
- Perfume
- Dyes
- Biocides, e.g. isothiazolinones, 2-bromo-2-nitro-1,3-propanediol
- Bleach systems consisting of bleaches, e.g. perborate, percarbonate, plus bleach activators, e.g. tetraacetylethylenediamine, plus bleach stabilizers
- Solubilizers, e.g. cumenesulfonates, toluenesulfonates, short-chain fatty acids, alkyl/aryl phosphates
- Solvents, e.g. short-chain alkyl oligoglycols, alcohols, such as ethanol or propanol, aromatic solvents, such as toluene or xylene, N-alkylpyrrolidones, for example N—($C_1$-$C_4$-alkyl)pyrrolidones, alkylene carbonates, for example $C_2$-$C_4$-alkylene carbonates
- Thickeners, such as, for example, polysaccharides and slightly crosslinked polycarboxylates (e.g. the Carbopol® brands from BF Goodrich).

These cleaners for hard surfaces are usually, but not exclusively, aqueous and are present in the form of microemulsions, emulsions or solutions. If they are to be present in solid form, standardizing agents as described above may additionally be used.

In the case of cleaners in tablet form, further additives are required. These are, for example, tableting assistants, e.g. polyethylene glycols having molar masses of >1000 g/mol or polymer dispersions. Tablet disintegrants, e.g. cellulose derivatives, crosslinked polyvinylpyrrolidone, crosslinked polyacrylates or combinations of acids, e.g. citric acid, with sodium carbonate, are also required.

Further possible applications of the compositions according to the invention are, for example, the adjustment of the rheological properties of formulations for the treatment of leather and textiles, of hydraulic fluids, of formulations for the coating of surfaces, of aqueous formulations which are used in building construction and civil engineering or of aqueous formulations which are used in crop protection.

The invention is explained in more detail below with reference to non-limiting examples.

EXAMPLES

1. Rheological investigations of compositions according to the invention

Component A.1:
Mixture consisting of about 70 mol % of $C_{16}$-$C_{18}$-alkyl-(O—($CH_2$)$_2$)$_4$—OP(=O)(OH)$_2$ and about 30 mol % of [($C_{16}$-$C_{18}$-alkyl-(O—($CH_2$)$_2$)$_4$)—O]$_2$P(=O)OH Component A.2:
27% strength by weight aqueous solution of a mixture consisting of 75 mol % of $C_{16}$-$C_{18}$-alkyl-(O—($CH_2$)$_2$)$_4$—OP(=O)$O_2$]$^{2-}$·2Na$^+$ and 25 mol % of Na$_2$HPO$_3$.

Component B:
25% strength solution of a reaction mixture, comprising the polymers obtained from the reaction of $C_{15}$-$C_{18}$-alkyl-[(O—($CH_2$)$_2$)$_{140}$])—OH (78% by weight), PEG 12 000 (20% by weight) and hexamethylene diisocyanate (2% by weight), in a mixture of 1,2-propanediol, isopropanol and water.

Component C:
n-octanol

Component D:
$C_{16}$-$C_{18}$-alkyl-[(O—($CH_2$)$_2$)$_{13}$])—OH (Lutensol® AT 13)

1.1 Aqueous composition, comprising 1.42% by weight of component (A.1), 0.80% by weight of component (B), 0.08% by weight of component (C), 0.30% by weight of component (D), 0.05% by weight of KOH and 3.00% by weight of KCl. After homogenization, the pH was adjusted to 4.1 with concentrated hydrochloric acid. The aqueous gel was measured in a cone-and-plate rheometer.

| Temperature [° C.] | Shear rate [s$^{-1}$] | Viscosity [mPa · s] |
|---|---|---|
| 25 | 13.2 | 170 |
| 25 | 30 | 150 |
| 25 | 100 | 160 |
| 25 | 300 | 100 |
| 50 | 6.6 | 415 |
| 50 | 30 | 220 |
| 50 | 100 | 115 |
| 50 | 300 | 60 |
| 70 | 6.6 | 145 |
| 70 | 30 | 90 |
| 70 | 100 | 50 |
| 70 | 300 | 25 |

1.2 Aqueous composition, comprising 1.52% by weight of component (A.1), 0.80% by weight of component (B), 0.08% by weight of component (C), 0.20% by weight of component (D), 0.05% by weight of KOH and 3.00% by weight of KCl. After homogenization, the pH was adjusted to 4.1 with concentrated hydrochloric acid. The aqueous gel was measured in a cone-and-plate rheometer.

| Temperature [° C.] | Shear rate [s$^{-1}$] | Viscosity [mPa · s] |
|---|---|---|
| 25 | 20.4 | >500 |
| 70 | 20.4 | 90 |

1.3 Aqueous composition, comprising 1.22% by weight of component (A.1), 0.80% by weight of component (B), 0.08% by weight of component (C), 0.50% by weight of component (D), 0.05% by weight of KOH and 3.00% by weight of KCl. After homogenization, the pH was adjusted to 4.1 with concentrated hydrochloric acid. The aqueous gel was measured in a cone-and-plate rheometer.

| Temperature [° C.] | Shear rate [s$^{-1}$] | Viscosity [mPa · s] |
|---|---|---|
| 25 | 20.4 | 20 |
| 70 | 20.4 | 95 |

1.4 Aqueous composition, comprising 1.42% by weight of component (AA), 0.80% by weight of component (B), 0.08% by weight of component (C), 0.30% by weight of component (D), 0.05% by weight of KOH and 3.00% by weight of KCl. After homogenization, the pH was adjusted to 7.5 with a semi-saturated aqueous NaOH solution. The aqueous gel was measured in a cone-and-plate rheometer.

| Temperature [° C.] | Shear rate [s$^{-1}$] | Viscosity [mPa · s] |
|---|---|---|
| 25 | 20.4 | <5 |
| 70 | 20.4 | <5 |

1.5 (Comparative example) Aqueous composition, comprising 1.42% by weight of component (A.1), 0.08% by weight of component (C), 0.30% by weight of component (D), 0.05% by weight of KOH and 3.00% by weight of KCl. After homogenization, the pH was adjusted to 4.1 with concentrated hydrochloric acid. The aqueous gel was measured in a cone-and-plate rheometer.

| Temperature [° C.] | Shear rate [s$^{-1}$] | Viscosity [mPa · s] |
|---|---|---|
| 25 | 20.4 | <5 |
| 70 | 20.4 | <5 |

1.6 Aqueous composition, comprising 6.88% by weight of component (A.2), 0.80% by weight of component (B), 0.08% by weight of component (C), 3.00% by weight of KCl. After homogenization, the pH was adjusted to 4.1 with concentrated hydrochloric acid. The aqueous gel was measured in a cone-and-plate rheometer.

| Temperature [° C.] | Shear rate [s$^{-1}$] | Viscosity [mPa · s] |
|---|---|---|
| 40 | 100 | 300 |
| 50 | 100 | 200 |
| 60 | 100 | 100 |
| 70 | 100 | 80 |
| 90 | 100 | 60 |

1.7 Aqueous composition, comprising 6.88% by weight of component (A.2), 0.80% by weight of component (B), 0.08% by weight of component (C) and 3.00% by weight of KCl. After homogenization, the pH was adjusted to 7.5. The aqueous gel was measured in a cone-and-plate rheometer.

| Temperature [° C.] | Shear rate [s$^{-1}$] | Viscosity [mPa · s] |
|---|---|---|
| 40 | 100 | <5 |
| 50 | 100 | <5 |
| 60 | 100 | <5 |
| 70 | 100 | <5 |
| 90 | 100 | <5 |

1.8 (Comparative example) Aqueous composition, comprising 6.88% by weight of component (A.2), 0.08% by weight of component (C) and 3.00% by weight of KCl. After homogenization, the pH was adjusted to 4.1 with concentrated hydrochloric acid. The gel was measured in a cone-and-plate rheometer.

| Temperature [° C.] | Shear rate [s$^{-1}$] | Viscosity [mPa · s] |
|---|---|---|
| 40 | 100 | 10 |
| 90 | 100 | <5 |

We claim:

1. A composition comprising:
   (A) at least one surfactant of the general formula (I)

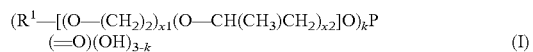
   (R$^1$—[(O—(CH$_2$)$_2$)$_{x1}$(O—CH(CH$_3$)CH$_2$)$_{x2}$]O)$_k$P(=O)(OH)$_{3-k}$     (I)

wherein the sequence of the alkyleneoxy units is arbitrary, each R$^1$ independently represents a moiety selected from the group consisting of linear and branched C$_{12}$-C$_{22}$-alkyl, C$_2$-C$_{22}$-alkenyl, C$_{12}$-C$_{22}$-alkynyl, (C$_{11}$-C$_{21}$-alkyl)carbonyl, (C$_{11}$-C$_{21}$-alkenyl)carbonyl and (C$_{11}$-C$_{21}$-alkynyl)carbonyl, k represents 1 or 2 and x1 and x2 each independently represent an integer of 0 to 20, the sum of x1 and x2 being a number of 1 to 20; and
   (B) at least one thickener comprising at least two hydrophobic groups R$^2$ which are linked to one another via a bridging hydrophilic group (α), wherein each R$^2$, independently represents a moiety selected from the group consisting of C$_8$-C$_{32}$-alkyl, C$_8$-C$_{32}$-alkenyl, C$_8$-C$_{32}$-alkynyl, cycloalkyl, aryl, and aryl-C$_1$-C$_{32}$-alkyl, which in each case may have up to 3 hydroxyl substituents;
   wherein the composition has a viscosity which is pH-dependent.

2. The composition according to claim 1, wherein the hydrophilic group (α) comprises at least two hydrophilic units (β).

3. The composition according to claim 2, wherein the hydrophilic units (β) comprise at least one polyether unit (γ) of the general formula (II)

   —[(O—(CH$_2$)$_2$)$_{y1}$(O—CH(CH$_3$)CH$_2$)$_{y2}$]—     (II)

where the sequence of the alkyleneoxy units is arbitrary and y1 and y2, independently of one another, are an integer of 0 to 300, the sum of y1 and y2 being a number of 10 to 300.

4. The composition according to claim 3, wherein the ratio of y1 to y2, averaged over the polyether units (y) of the general formula (II) which are present, is at least 2:1.

5. The composition according to claim 4, wherein y2 in the polyether units (γ) of the general formula (II) which is present is 0.

6. The composition according to claim 3, wherein the sum of y1 and y2, averaged over the polyether units (γ) of the general formula (II) which are present, has a value of 2 to 200.

7. The composition according to 2, wherein at least two of the hydrophilic units (β) are linked to one another via a bridging group (γ).

8. The composition according to claim 7, wherein the bridging group (γ) has at least one terminal structural unit of the formula —OC(=O)NH—.

9. The composition according to claim 2, wherein the hydrophilic units (β) are each independently selected from the group consisting of polyether units and polyvinyl alcohol units.

10. The composition according to claim 1, wherein the ratio of x1 to x2, averaged over the surfactants of the general formula (I) which are present, is at least 2:1.

11. The composition according to claim 10, wherein x2 in the surfactants of the general formula (I) which are present is 0.

12. The composition according to claim 1, wherein at least one surfactant of the general formula (I) comprises a compound of the general formula (I.a)

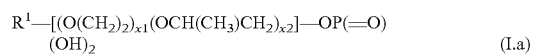
    R$^1$—[(O(CH$_2$)$_2$)$_{x1}$(OCH(CH$_3$)CH$_2$)$_{x2}$]—OP(=O)(OH)$_2$     (I.a)

Wherein the sequence of the alkyleneoxy units is arbitrary, R$^1$ represents a moiety selected from the group consisting of linear or branched C$_{12}$-C$_{22}$-alkyl, C$_{12}$-C$_{22}$-alkenyl, C$_{12}$-C$_{22}$-alkynyl, (C$_{11}$-C$_{21}$-alkyl)carbonyl, (C$_{11}$-C$_{21}$-alkenyl)carbonyl and (C$_{11}$-C$_{21}$-alkynyl)carbonyl and x1 and x2, independently of one another, are an integer of 0 to 20, the sum of x1 and x2 being a number of 1 to 20.

13. The composition according to claim 12, wherein at least 50% of the surfactants of the general formula (I) which are present comprise compounds of the general formula (I.a).

14. The composition according to claim 1, wherein the R$^1$ groups have an average of not more than one branch.

15. The composition according to claim 1, wherein each R$^1$ independently represents a moiety selected from the group consisting of palmityl, stearyl, oleyl, linoleyl, arachidyl, gadoleyl, behenyl, erucyl, isostearyl, 2-hexyldecyl, 2-heptyldecyl, 2-heptylundecyl and 2-octyldodecyl.

16. The composition according to claim 1, wherein the sum of x1 and x2, averaged over the surfactants of the general formula (I) which are present, has a value of 1 to 10.

17. The composition according to claim 1, wherein the sum of x1 and x2, averaged over the surfactants of the general formula (I) which are present, has a value of 3 to 9.

18. The composition according to claim 1, wherein the at least two hydrophobic groups R$^2$ each independently represent a moiety selected from the group consisting of linear or branched C$_{12}$-C$_{22}$-alkyl, C$_{12}$-C$_{22}$-alkenyl or 2-hydroxy(C$_{12}$-C$_{22}$-alk-1-yl).

19. The composition according to claim 1, wherein the thickeners (B) present each have from 2 to 6 hydrophobic groups R$^2$.

20. The composition according to claim 1, wherein the thickeners (B) present have on average a molecular weight in of 3,000 to 50,000 g/mol.

21. The composition according to claim 1, further comprising (C) at least one C$_6$-C$_8$-monoalcohol.

22. The composition according to claim 1, further comprising (D) at least one nonionic surfactant of the general formula (III)

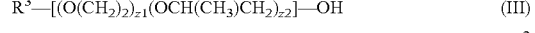
    R$^3$—[(O(CH$_2$)$_2$)$_{z1}$(OCH(CH$_3$)CH$_2$)$_{z2}$]—OH     (III)

wherein the sequence of the alkyleneoxy units is arbitrary, R$^3$ is selected from C$_{12}$-C$_{22}$-alkyl, C$_{12}$-C$_{22}$-alkenyl, C$_{12}$-C$_{22}$-alkynyl, (C$_{11}$-C$_{21}$-alkyl)carbonyl, (C$_{11}$-C$_{21}$-alkenyl)carbonyl and (C$_{11}$-C$_{21}$-alkynyl)carbonyl and z1 and z2, independently of one another, are an integer of 0 to 20, the sum of z1 and z2 being a number of 1 to 20.

23. The composition according to claim 1, further comprising (E) at least one water-miscible solvent having a molecular weight of less than 400 g/mol.

24. The composition according to claim 1, further comprising (F) at least one water-miscible base.

25. A method comprising providing an aqueous composition and adjusting a rheological property of the aqueous composition with the composition according to claim 1.

26. The method according to claim 25, wherein the aqueous composition is selected from the group consisting of ground drilling fluids, detergents, cleaning agents, leather treatment agents, textile treatment agents, hydraulic fluids, agricultural formulations, coating compositions, building construction formulations and civil engineering formulations.

27. A process comprising: providing an acid gelling agent or drilling fluid comprising a composition according to claim 1, and treating an underground geological formation with the acid gelling agent or drilling fluid.

* * * * *